US006824776B2

(12) United States Patent
Rolison et al.

(10) Patent No.: US 6,824,776 B2
(45) Date of Patent: Nov. 30, 2004

(54) SILICA MESOPOROUS AEROGELS HAVING THREE-DIMENSIONAL NANOARCHITECTURE WITH COLLOIDAL GOLD-PROTEIN SUPERSTRUCTURES NANOGLUED THEREIN

(75) Inventors: Debra R. Rolison, Arlington, VA (US); Jean M. Wallace, Alexandria, VA (US); Jeremy J. Pietron, Washington, DC (US); Jane K. Rice, Fairfax, VA (US); Rhonda M. Stroud, Washington, DC (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 41 days.

(21) Appl. No.: 10/414,570

(22) Filed: Apr. 16, 2003

(65) Prior Publication Data

US 2004/0209338 A1 Oct. 21, 2004

(51) Int. Cl.[7] .................................................. C08J 9/36
(52) U.S. Cl. ................. 424/141.1; 106/122; 424/145.1; 424/146.1; 521/84.1
(58) Field of Search ........................ 523/219; 106/122; 424/141.1, 145.1, 146.1; 521/84.1

(56) References Cited

U.S. PATENT DOCUMENTS

| 5,292,801 A | 3/1994 | Avnir et al. |
| 5,298,135 A | 3/1994 | Geoghegan |
| 5,650,333 A | 7/1997 | Holtlund et al. |
| 6,277,489 B1 * | 8/2001 | Abbott et al. ............... 428/403 |
| 6,492,014 B1 | 12/2002 | Rolison et al. |

OTHER PUBLICATIONS

Daryl K. Eggers et al., "Molecular confinement influences protein structures and enhances thermal protein stability," Protein Science, 2001, 10, 250–261.
B. Dunn et al., "Strategies for Encapsulating Biomolecules in Sol–Gel Matrices," Acta Mater., 1998, 46, 737–741.
Rimple B. Bhatia et al., "Aqueous Sol–Gel Process for Protein Encapsulation," Chem. Mater., 2000, 12, 2434–2441.
Christopher R. Lloyd et al., "Protecting Heme Enzyme Peroxidase Activity from H2O2 Inactivation by Sol–Gel Encapsulation," Langmuir, 2000, 16, 9092–9094.
Lisa M. Ellerby et al., "Encapsulation of Proteins in Transparent Porous Silicate Glasses Prepared by the Sol–Gel Method," Science, 1992, 225, 1113–1115.

Jonathan W. Aylott et al., "Optical Biosensing of Gaseous Nitric Oxide Using Spin–Coated Sol–Gel Thin Films," Chem. Mater., 1997, 9, 2261–2263.
Catherine A. Morris et al., "Silica Sol as a Nanoglue: Flexible Synthesis of Composite Aerogels," Science, 1999, 284, 622–624.
Nicholas Leventis et al., "Durable Modification of Silica Aerogel Monoliths with Fluorescent 2,7–Diazapyrenium Moieties. Sensing Oxygen near the Speed of Open–Air Diffusion," Chem. Mater., 1999, 11, 2837–2845.
Christine D. Keating et al., "Protein:Colloid Conjugates for Surface Enhanced Raman Scattering: Stability and Control of Protein Orientation," J. Phys. Chem. B, 1998, 102, 9404–9413.
Michele L. Anderson et al., "Colloidal Gold Aerogels: Preparation, Properties, and Characterization," Langmuir, 1999, 15, 674–681.
Michele L. Anderson et al., "Tailoring Advanced Nanoscale Materials Through Synthesis of Composite Aerogel Architectures," Adv. Eng. Mat., 2000, 2, 481–488.
Michael S. Wong et al., "Assembly of Nanoparticles into Hollow Spheres Using Block Copolypeptides," Nano Lett., 2002, 2, 583–587.
Christine D. Keating et al., "Heightened Electromagnetic Fields between Metal Nanoparticles: Surface Enhanced Raman Scattering from Metal–Cytochrome c–Metal Sandwiches," J. Phys. Chem. B, 1998, 102, 9414–9425.
Aimin Yu et al., "Nanostructured Electrochemical Sensor Based on Dense Gold Nanoparticle Films," Nano Lett., 2003, 3, 1203–1207.

* cited by examiner

*Primary Examiner*—Morton Foelak
(74) *Attorney, Agent, or Firm*—John J. Karasek; Rebecca L. Forman

(57) ABSTRACT

This disclosure describes the first viable non-enzyme protein encapsulated within an aerogel. In this, a large excess of cyt. c is added to a commercial buffered Au sot solution ( ) which results in the formation of a gold~protein-protein superstructure in the absence of separation techniques which destroy the superstructure.

The gold~protein-protein superstructure is then nanoglued into a silica framework during the sol to gel transition. To form the gel, the Au-cyt. c superstructure in buffered medium is added to a silica sol and the composite gels are washed with acetone followed by liquid carbon dioxide and then supercritically dried to form the aerogel.

The biocomposite aerogels have a multiplicity of applications particularly in the realm of sensing and energy transformation.

14 Claims, 4 Drawing Sheets

SILICA MESOPOROUS AEROGELS HAVING THREE-DIMENSIONAL NANOARCHITECTURE WITH COLLOIDAL GOLD-PROTEIN SUPERSTRUCTURES NANOGLUED THEREIN

BACKGROUND OF THE INVENTION

1. Field of the Invention

The disclosed invention relates to aerogels and specifically to silica aerogels having three-dimensional nanoarchitecture with colloidal gold~protein superstructures nanoglued therein. The disclosure describes methods for making the composite bioaerogels and their physical and chemical characteristics.

2. Description of Background Art

Much attention has been focused on immobilization of biomolecules in silicate glass formed by the sol-gel method, Eggers et al., *Protein Sci.* 2001, 10, 250–261. The process involves hydrolyzing an alkoxide to produce a sol, which then undergoes polycondensation to form a gel. Biomolecules are immobilized by being entrapped in the gel during the sol-to-gel transition. The sol-gel materials offer advantages over more traditional organic polymers for biomolecule entrapment in that these materials have increased mechanical strength, chemical stability, biocompatibility, and resistance to microbial attack.

While one can encapsulate a variety of biomolecules (enzymes, proteins, antibodies, cells) in sol-gel-derived matrices, the earliest reported bio/silicate-gels had only 30% activity as prepared using the conventional, alcohol-rich sol-gel preparation. Bioactivity of caged biomolecules rose to 75–95% upon the advent of the Dunn procedure, Dunn et al., *Acta Mater.* 1998, 46, 737–741, which uses less alcohol and provides better buffering of the sol. Traditionally when biomolecules have been incorporated into sol-gel-derived materials, the resultant gels are either kept wet (forming hydrogels) or are dried from aqueous conditions (forming xerogels) resulting in pore collapse of the material and long-sensing response times. The hydrogels are not ideal for real-world sensing either, in that they must be kept wet, stored at 4° C., and the long-term stability of the encapsulated biomolecule has not been investigated. The longest reported lifetime of these materials is approximately a month when stored at 4° C.

Heme proteins, such as horseradish peroxidase, Bhatia et al., *Chem. Mater.* 2000, 12, 2434–2441, cytochrome c (cyt. c) Lloyd et al., *langmuir* 2000, 16, 9092–9094 and myoglobin, Ellerby et al., *Science* 1992, 257, 1113–1116, have been extensively studied in sol-gel encapsulation. These proteins retain their spectroscopic properties and chemical functions of oxidation and reduction, ligand binding, or biocatalysis upon encapsulation. In one case, cyt. c was encapsulated into a sol-gel and absorbance-based spectral shifts were used to monitor binding of nitric oxide. Unfortunately, the sensor reaction is reported to have taken two hours to reverse, making dynamic measurements impractical, Aylott et al., *Chem. Mater.* 1997, 9, 2261–2263.

BRIEF SUMMARY OF THE INVENTION

We have encapsulated heme protein into a silica framework, facilitated by formation of a protein—protein superstructure nucleated in the liquid phase by colloidal gold. In solution, the protein is known to specifically adsorb via surface lysine residues to the surface of the Au with the heme pocket toward the metal. We posit that this adsorption-induced presentation of the back face of the protein to the protein-buffer medium leads to "tail—tail"-directed protein-protein assembly, alternating with "head—head" protein-protein association, to leave essentially no unassociated protein in the buffered medium. The 'outer skin' of protein acts as a protective barrier and stabilizes the proteins within the superstructure against denaturants, including those arising during synthesis and processing of the silica nanoarchitecture. The gold~protein-protein superstructure of the invention is nanoglued into the silica framework during the sol-to-gel transition. The wet gel is dried from supercritical fluid (SCF), forming a mesoporous aerogel, which permits true gasphase sensing with facile molecular transport into the biomolecule-modified three-dimensional nanoarchitecture of the aerogel. Although gold is described specifically throughout this disclosure, it is to be understood that silver, platinum, palladium, copper, and nickel may take the place of gold in this invention.

DETAILED DESCRIPTION OF THE INVENTION

The approach described in this invention is to solve the problems described above (i.e., liquid/thermal conditions or sluggish temporal signatures) for biomolecule-silica composite gels. The approach is to nanoglue biomolecules, and specifically heme proteins within aerogels. The aerogel network prevents bio-aggregation and protects against denaturants, as do the hydrogels and xerogels mentioned above. But the high, three-dimensional continuous porosity and ultralow density of the biomolecule-silica nanoarchitecture facilitate analyte flux, with rates approaching self-diffusion in pure media. To date, there are few reports of bioaerogels in the literature. All examples describe either the immobilization of lipase, one of the 'heartiest' of enzymes, which catalyzes reactions in boiling organic solvents or post-SCF-introduced bacteria. Interestingly, improved activity and stability of the enzymes is reported within the aerogels.

The Rolison group has synthesized and characterized nanostructured, highly porous silica aerogels and used silica sol to 'nanoglue' a wide range of guests into silica nanoarchitectures, Morris et al. *Science* 1999, 284, 622–624, this reference is incorporated herein by reference in its entirety. These silica-based composite gels retain the porosity and surface area of the aerogel and add the known properties of the guest. We have demonstrated facile molecular transport to the guests within the silica matrix, Leventis et al., *Chem. Mater.* 1999, 11, 2837–2845.

Our earlier efforts to create bioactive nanoarchitectures by adding silica sol to solutions of cyt. c in buffer led to cyt. c-silica wet composite gels that retained only moderate configurational integrity for the protein. The Soret band of cyt. c was noted to both red- and blue-shift between samples dried from hexane as ambigels; however the direction and size of these shifts were not reproducible and often unpredictable. Also, the overall quality of thin films of silica aerogels is poor, and introduction of a biological moiety did not greatly enhance the quality of the resultant biocomposite thin films.

Figure 1:
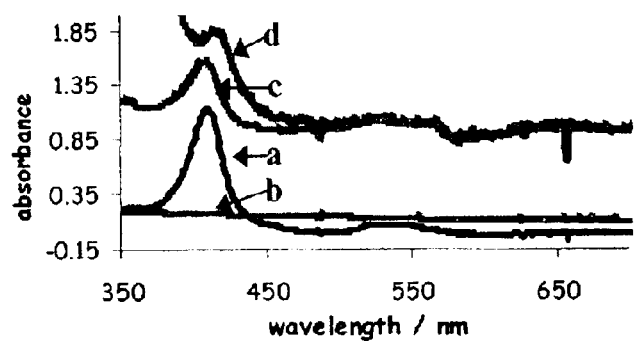
FIG. 1. Visible spectra of cytochrome c in various media: (a) cyt. c in buffer solution; (b) cyt. c-$SiO_2$ composite aerogel; Au-cyt. c-$SiO_2$ in (c) air and (d) with bound NO.

Furthermore, when the cyt. c-silica composite gels were supercritically dried to produce composite aerogels, the visible absorption was totally lost, indicating that not only was the heme destroyed, but that the metal-porphyrin coordination was destroyed as well (see trace b in FIG. 1). In an effort to stabilize the heme crevice of the protein during the aerogel processing, the pre-gel superassemblies, nucleated by colloidal gold, were doped into the silica framework during gelation.

One approach to control the degree of unfolding (i.e., stabilization of the heme crevice) during the gel formation and processing is through the use of Au colloids. Colloidal Au has been used as a platform to bind many biological molecules, including proteins. Prior work demonstrated that a submonolayer-to-monolayer coverage of cyt. C can be chemisorbed to colloidal Au with no detrimental effects to the protein conformation, Keating et al., *J. Phys. Chem. B* 1998, 102, 9404–9413.

Cytochrome c and colloidal 10-nm Au sol are pre-mixed in buffered solution to form a Au~protein superstructure and then introduced into the silica sol, prepared as described below. The resultant biocomposite gels are washed with acetone and liquid carbon dioxide and then supercritically dried forming aerogels. Unlike the aerogels in which no Au is present, a Soret band is evident, indicating that the stabilized protein 'survives' the solvent-replacement steps and the drying process. These Au~cyt. c-silica composite aerogels retain the spectral signature of an active heme (compare FIG. 1a to FIG. 1c). Bioactivity is further demonstrated by the ability of the aerogel-incorporated cyt. c to bind gas-phase NO with a shift in peak maximum comparable to that seen for binding of NO by cyt. c in buffer (see FIG. 1d).

Interestingly, the ratio of cyt. c to Au in these gels is much greater than a monolayer, and are on the order of 10,000 protein molecules to one gold particle. Literature reports of biomolecules bound to metal colloids are of a monolayer or less, where excess protein is removed by centrifugation. How does the presence of relatively few Au colloids result in $\geq 80\%$ of the protein molecules remaining viable after the gelation, solvent replacement, and drying processes, while 0% of protein is viable without colloidal Au present?

We propose that some form of protein—protein superstructure must form in which the colloidal Au acts as a nucleating site for suprarnolecular assembly of protein. The monolayer of cyt. c that specifically adsorbs to the Au nanoparticle "organizes" the excess cyt. c in the buffer. The protein is known to specifically adsorb to Au via surface lysine residues with the heme pocket toward the metal (for example, ~35 cyt. c molecules will form a monolayer on 10-nm Au). We propose that this adsorption-induced presentation of the back face of the protein to the medium leads to "tail—tail"-directed protein-protein assembly, alternating with "head—head"-directed protein-protein association, to leave essentially no unassociated cyt. c in the buffered medium. We estimate that ~100-nm objects form in the microheterogeneous buffer medium, because 10,000~3-nm cyt. c molecules, if cubic close-packed, would be 60 nm on a side.

Figure 2:
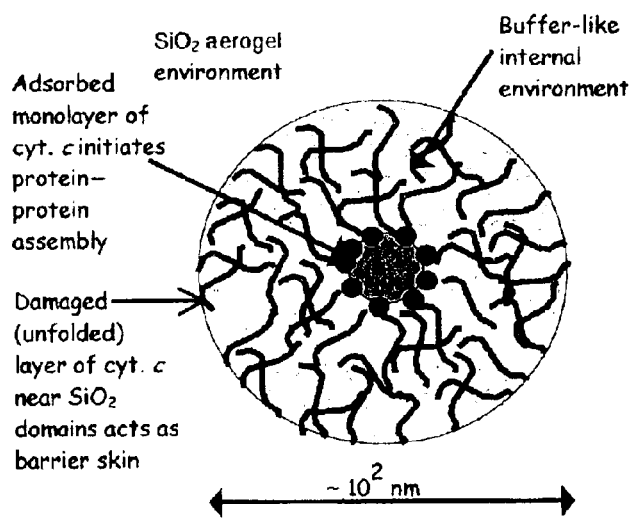
FIG. 2. Cross-sectional model of proposed Au~protein-protein superstructure. In this figure, the protein monolayer is absorbed on the gold colloid and serves as the template upon which the protein-protein superstructure is assembled. Unfolded or 'damaged' layers of protein near the $SiO_2$ domain act as a barrier skin to protect the superstructure.

The stabilized biocomposite nanoarchitecture is formed when silica sol nanoglues the Au~cyt. c superstructures into the gel. Within the Au~cyt. c superstructure, the inner cyt. c experiences a buffer-like environment (thereby protected from sol-gel and SCF processing), while boundary-sited cyt. c is damaged or unfolded and acts as an outer barrier or "skin". A model of the proposed Au~cyt. c superstructure is shown in FIG. 2.

Figure 3:
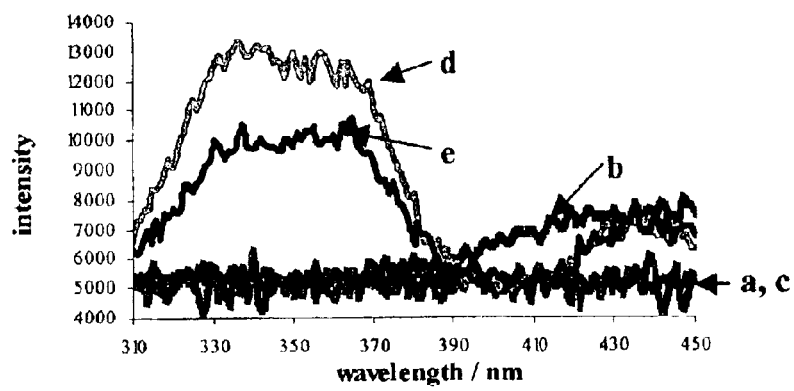
FIG. 3. Fluorescence emission for the trytophan-59 residue of cyt. c in solutions with and without guanidinium hydrochloride (GnHCl): (a) cyt. c solution; (b) Au sol; (c) Au~cyt. c composite; (d) cyt. c in 5 M GnHCl; (e) Au-cyt. c composite in 5 M GnHCl.

Characterization of the Au~cyt. c superstructure and biocomposite aerogel supports this model. Protein conformation, as monitored by the wavelength position of the Soret band, indicates that cyt. c in both the Au~cyt. c superstructure and Au~cyt. c-SiO$_2$ composite aerogel retains its folded, native state, and can bind gas-phase NO as mentioned above (FIG. 1). Fluorescence emission from the tryptophan-59 residue of cyt. c critically depends on the conformational integrity around the heme and is used to indicate local perturbations. Monitoring the chemical unfolding of cyt. c by guanidinium hydrochloride (GnHCl) indicates that the protein is stabilized in the presence of 10-nm Au relative to cyt. c dissolved in buffer (FIG. 3).

Figure 4:
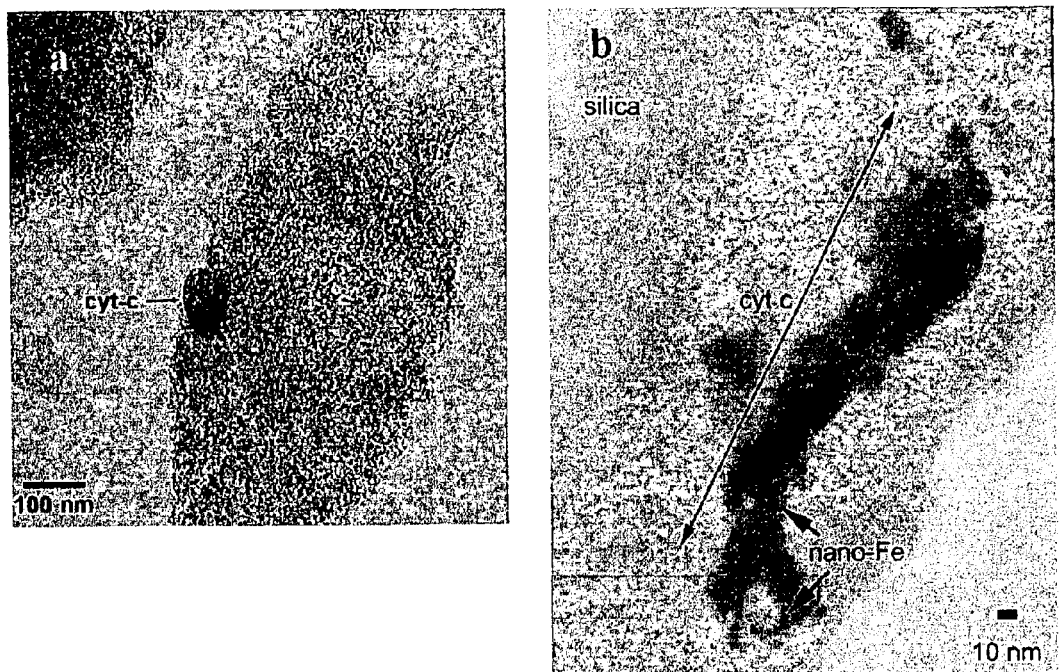
FIG. 4. Transmission electron micrographs of Au~cyt. c structures within silica aerogel. Spherical protein superstructures are observed (a) in the biocomposite aerogels when the cyt. c buffer solution is added to the gold sol with immediate stirring. Oblate protein superstructures are observed (b) if the two media are mixed without immediate stirring.
Figure 5:
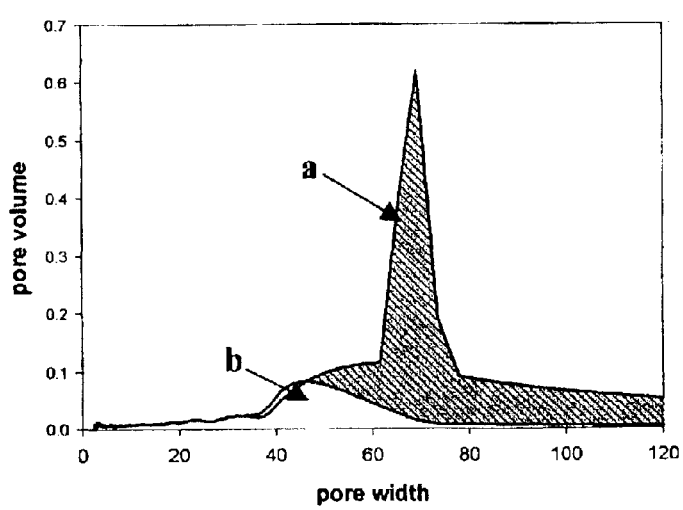
FIG. 5. Nitrogen physisorption data, modeled with Density Function Theory, for calcined samples (at 600° C.) of (a) Au~cyt. c-$SiO_2$ aerogels and (b) Au-$SiO_2$ aerogelsgray area represents the additional free volume obtained after pyrolysis of the protein.

In FIG. 4, dynamic light scattering indicates that a freshly prepared medium of Au sol plus cyt. c is highly scattering (on a lengthscale of 102 nm) and transmission electron microscopy shows ~102-nm spherical or oblate cyt. c structures within the silica aerogel. Using N$_2$ physisorption to examine the pore structure of Au~cyt. c-SiO$_2$ composite aerogels calcined to 600° C., where all organic molecules (including cyt. c) are removed through pyrolysis, we note a large increase in pore volume at pore sizes >65 nm (FIG. 5).

The UV and visible circular dichroic (CD) spectra provide information on the integrity of the protein secondary structure. Characteristic CD spectra indicating alpha helices are seen in the UV region (not shown) and in the weaker CD spectra of the Soret band for the biocomposite solution.

Figure 6:
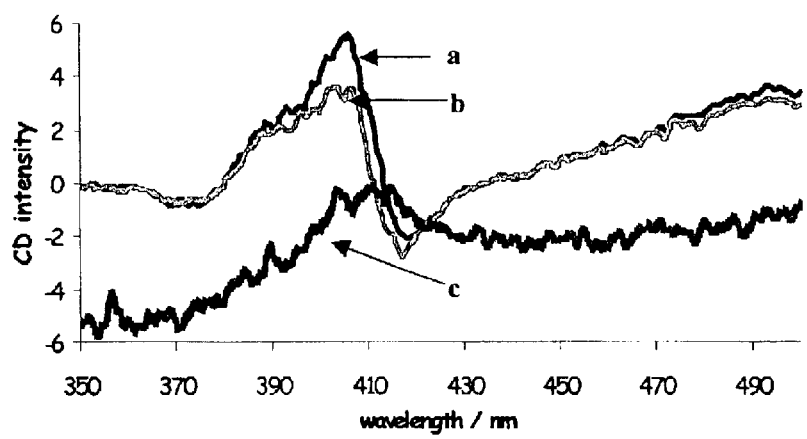
FIG. 6. Circular dichroic spectra (CD) for Au~cyt. c superstructures; (a) cyt. c in buffer; (b) Au~cyt. c superstructure in solution; (c) Au~cyt. C-$SiO_2$ composite aerogel.

The circular dichroic (CD) spectra for Au~cyt. c superstructures in buffer medium yield evidence of a 'healthy' tertiary protein (FIG. 6). The Soret CD spectra exhibit a positive and negative (derivative) shape, which indicates an intact cyt. c protein within the superassembly. This shape converts to a positive signal centered at the inflection when secondary structures within the protein weaken or are partially unfolded as is seen in the spectra for the Au~cyt.c-SiO$_2$ biocomposite aerogel (FIG. 6). It is known that binding of cyt. c to lipid membranes or micelles induces a partial unfolding or disruption of the protein's compact structure, which is marked by a loss of tertiary structure in the Soret CD spectra. This binding is driven by both electrostatic and hydrophobic lipidprotein interactions.

While very little literature exists on CD of proteins in microheterogeneous media, we interpret our findings in light of the characteristics of cyt. c-lipid binding. Cytochrome c in buffered medium and Au~cyt. c superstructure in solution have similar "derivative" signatures with positive and negative components, and the composite is only slightly less intense. However, the Soret CD spectra of the Au~cyt. c-SiO$_2$ composite aerogel indicates a single positive band (offset at ~6) similar to that of an unfolded protein in solution. This chiral increase may be explained by the fact that chiral signals are magnified at surface interfaces.

We propose that the Soret CD spectra we obtained for the biocomposite aerogel reflects the boundary species or outer sacrificial skin of our model superstructure. That is, the resultant spectra reveal that the outer portion of the superstructure incorporated within the aerogel, and presumably strongly associated with silica colloids, is unfolded and lacks tertiary structure, but possesses alpha helical characteristics similar to native protein in solution.

Figure 7:
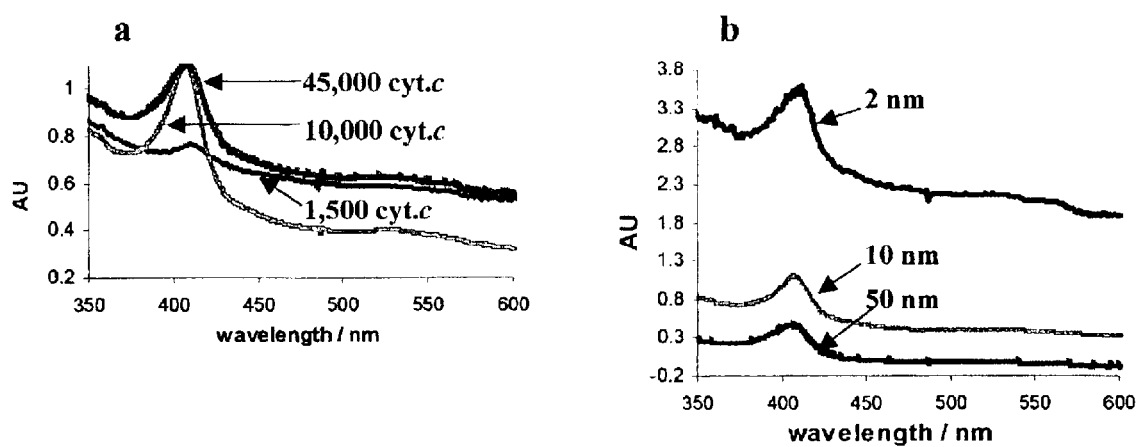
FIG. 7. Visible spectra of cytochrome c in Au~cyt. c-$SiO_2$ dry aerogels where (a) the ratio of Au~cyt. c is varied; and (b) the size of the Au colloid is varied.

While much evidence has been presented here for 10,000 cyt. c molecules bound to one 10-nm Au colloid, one can adsorb, and subsequently encapsulate, a great number of cyt. c molecules within the superstructure. FIG. 7a shows an example of the visible spectra for Au~cyt. c-Si 2 aerogels where several layers of cyt. c are bound to 10-nm colloidal Au, e.g., the protein:Au ratio varies from ~1,500:1 to 45,000:1. For simplicity, only one case (10,000 cyt. c:1 Au) has been thoroughly discussed here. Similarly, the size of the colloidal Au can be altered and the silica aerogel biocomposite formed. FIG. 7b also shows several examples where the protein-Au conjugate was formed with either 2-, 10-, or 50-nm colloidal Au and subsequently doped into an-about-to-gel silica sol. Clearly this range of Au colloid size has little effect upon the folding and stabilization of the protein as indicated by the Soret band. This stabilization and encapsulation methodology can be applied to a variety of biomolecules, both heme and non-heme proteins, both enzymes and non-enzymes; e.g., blue copper proteins and photosynthetic reaction centers.

Figure 8:
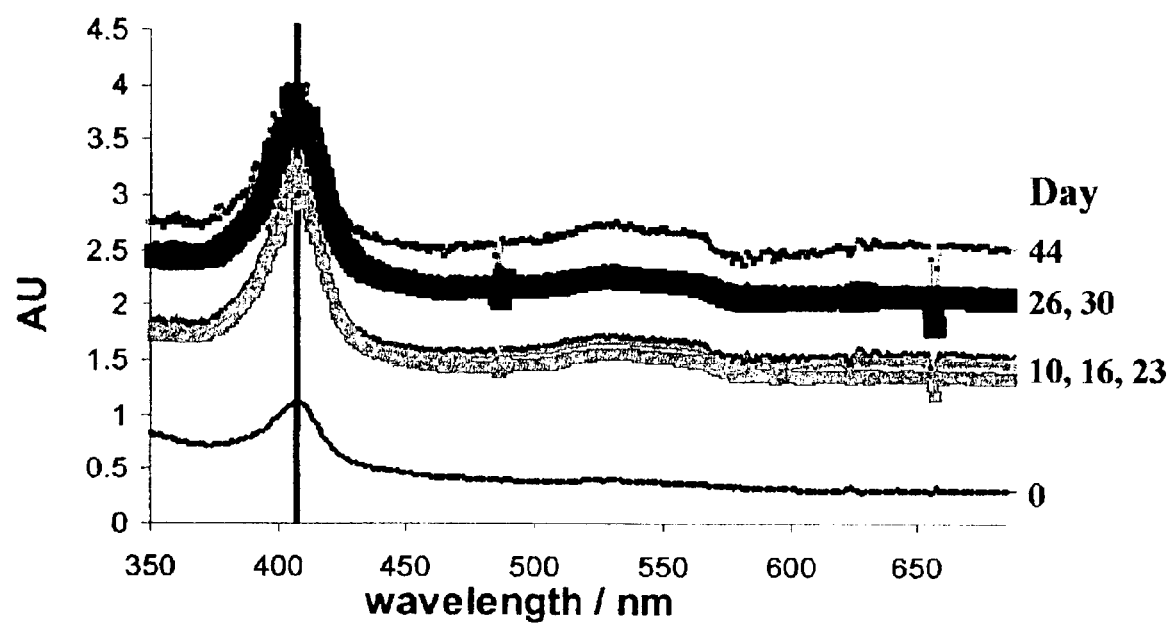
FIG. 8. Visible spectra of cytochrome c in Au~cyt. c-$SiO_2$ dry aerogels where the gels were stored at room temperature and at high (i.e., 100%) constant relative humidity. Monitoring the Soret band as a function of time, indicates that the protein retains its configuration for at least six weeks under these conditions.

Unlike previous bio sol-gels, where the longest lifetime of the encapsulated biomolecule was one month at 4° C., these dry biocomposite aerogels remain viable for up to 6 weeks at room temperature as seen in FIG. 8. The silica matrix itself presents many of the advantages observed in the hydro- and xero-gels previously studied (mechanical strength, chemical stability, biocompatibility, and resistance to microbial attack) and the high porosity and ultralow density of the biomolecule-silica nanoarchitecture allows for rapid analyte flux and detection. Furthermore, these biocomposite gels offer added stability at a greater range of temperatures, making them more real-world applicable.

Had we not "frozen" the Au+cyt. c microheterogeneous medium by nanogluing with silica sol, we would never have known such superstructures were created. We can find no report of such colloid-directed protein superstructures in the literature. Addition of a large excess of cyt. c to commercial Au sol (results in formation of a protein-protein superstructure, in the absence of any separation technique. We believe that these assemblies were also formed in previous studies, but that the shear forces of centrifugation destroyed the structure. The stabilization of the Au~cyt. c superstructure in buffer is evident from the resistance to chemical denaturation with GnHCl.

While a plethora of literature are available concerning biomolecule characterization within various xerogel materials, there are limited reports describing similar studies conducted within aerogels. We have produced the first viable non-enzyme protein encapsulated within an aerogel, capable of rapid gas-phase sensing, further demonstrating that the protein is stabilized via the gold nanoparticle-directed assemblies, as shown when incorporated within porous nanoarchitectures. These biocomposite aerogels have a multitude of applications, particularly in the realm of sensing and energy transformation.

No reported cases of non-enzyme protein-aerogel composite materials can be found in the literature, nor are there reports of protein-protein self-assembled superstructures as nucleated via colloidal metal nanoparticles.

However, many examples exist in the literature of protein-protein conjugates and of formation of biomolecular devices. For example, an artificial molecular device was fabricated by crosslinking cyt. c with N-succinimidyl-3-(2-pyridyldition)propionate, such that the modified protein adsorbed to a planar gold surface, followed by adsorption of green fluorescent protein to the cyt. c surface. J. -W. Choi, S. -J. Park, Y. -S. Nam, W. H. Lee, M. Fujihira, *Colloids Surf. B: Biointerfaces* 2002, 23, 295–303.

Experiments

Reagents Cytochrome c (horse heart, Type VI) was obtained from Sigma Aldrich and used without further purification. The concentration of cytochrome solutions was calculated from the visible spectra (HP UV 8453) using an extinction coefficient of 106100 M$^1$ cm$^{-1}$ for the Soret band. Guanidinium hydrochloride (GnHCl) was obtained from Sigma Aldrich. All reagents were used as received, unless otherwise noted, and water for all experiments was 18 MΩcm (Barnstead NANOpure). Gold~Protein Biocomposite 10-nm colloidal gold sol (BBlnternational) was added with or without stirring to the stock cytochrome c solution (~0.7–0.9 mM, in a pH 7, 50 mM phosphate buffer) in a 1:10,000 ratio (i.e., 2.5 mL of colloidal Au to 500 μL of cytochrome). Either type of mixture was then stirred for a minimum of 10 minutes and no separation techniques (i.e., centrifugation) were employed. The size of the colloidal gold sol was also varied from 2, 5, 20, and 50 nm. The ratio of the number of protein molecules to gold colloid was also varied from about 1,500 to about 45,000. Preparation of the silica sol The base-catalyzed silica sol preparation was similar to that previously described. First, 1.89 g of tetramethoxysilane (TMOS, Alfa AESAR, 98%) and 2.88 g of methanol (Mallinckrodt) were combined in a plastic beaker. Then, 0.75 g of water, 3 g of methanol and 5 μL of 28% NH$_4$OH (99.99+%, Aldrich) were added to a second beaker. The first beaker (containing the TMOS) was added to the second and the contents were stirred for at least 15 minutes. At this time, the Au~cytochrome c mixture was added to the silica sol in a 1:6 volume ratio and mixed for up to 2 minutes. The silica-Au~cytochrome mixture was poured into cylindrical molds (13×57 mm) and sealed with parafilm. The gels were allowed to age for 1 day at 4° C. The aged gels were then transferred to glass vials where they were first rinsed with ethanol (Warner-Grahamn Company) at least 4 times over a day and half. The gels were then rinsed with acetone (Fisher Scientific) at least 8 times over 3 to 4 days.

The gels were then loaded into a supercritical dryer (Fisons Bio-Rad E3000), where the acetone was replaced with liquid $CO_2$. The liquid $CO_2$ was brought above its critical temperature and pressure ($T_c$=31° C.; $P_c$=7.4 MPa) and released to dry the gels. Gel shrinkage during the drying process was minimal. The gels were a translucent pink.

Physical Characterization UV-visible spectra for the biocomposite solution and Au~cyt. c-$SiO_2$ aerogels were obtained using an HP 8453 diode single array spectrophotometer. Circular dichroic spectra were conducted with a JASCO 720 spectrophotometer. Data were collected in the both the UV and Soret regions.

Fluorescence measurements were obtained with a Fluorolog Spex (1681 0.22-m spectrometer and 1680 0.22-m double spectrometer). Emissions scans of 310-to-450 nm were recorded after excitation at 295 nm. All solutions examined by fluorescence (cytochrome c and Au before formation of biocomposite; aqueous buffer, aqueous GnHCl; and pure water), were filtered with Teflon 0.45-$\mu$m syringe filters (Fisherbrand). After filtering, the biocomposite was mixed as mentioned above. Initial emission scans were recorded for the Au~cyt. c composite and for a cyt. c control, and then the solutions were spiked with GnHCl, and additional emission scans were recorded for the unfolded protein.

Nitrogen physisorption measurements (at 77 K) of the monoliths were obtained using a Micromeritics ASAP 2010 accelerated surface area and porosimetry system, after the samples were calcined to 600° C. Samples analyzed by TEM were prepared by pipetting a solution of crushed Au~cytochrome c-$SiO_2$ aerogel composite in acetone onto carbon-coated TEM holey grids. A JEOL 2010F TEM was used for the analysis.

What is claimed is:

1. A method for making a silica mesoporous aerogel having three-dimensional nanostructure with a colloidal metal~protein biocomposite nanoglued therein, comprising:
   A. forming a metal~protein biocomposite by mixing together said protein and said colloidal metal;
   B. forming a silica sol by mixing together a catalyst and a silicon alkoxide;
   C. forming a gel by mixing together said silica sol and said biocomposite and allowing said sol to gel;
   D. extracting and supercritically drying said gel with carbon dioxide to form said silica aerogel with said metal~protein biocomposite nanoglued therein.

2. A method according to claim 1, wherein said protein is selected from the group consisting of heme and non-heme proteins or enzymes comprising cytochrome c, blue copper proteins, and proteins, or photo synthetic reaction centers.

3. A method according to claim 2, wherein said protein is a non-enzyme protein.

4. A method according to claim 2, wherein said protein is cytochrome c.

5. A method according to claim 1, wherein said silicon alkoxide is tetramethoxysilane.

6. A method according to claim 1, wherein said catalyst is either a basic or an acidic chemical reagent.

7. A method according to claim 1, wherein said colloidal metal is selected from the group consisting of gold, silver, platinum, palladium, copper or nickel.

8. A method according to claim 7, wherein said metal is colloidal gold in the size range of 2–50-nm.

9. A method according to claim 8, wherein said colloidal gold is 10-nm gold particles.

10. A method according to claim 1, wherein said metal colloid is gold and said protein is cytochrome c.

11. A method according to claim 10, wherein the gold-to-protein ratio in said aerogel is on the order of one gold particle to 10,000 protein molecules.

12. A method according to claim 10, wherein the gold-to-protein ratio in said aerogel is one colloidal gold to about 1,500 to about 45,000 protein molecules.

13. A method according to claim 1, wherein said protein in said aerogel is >80% viable.

14. A method for making a silica mesoporous aerogel having three-dimensional nanoarchitecture with a colloidal gold-cytochrome c superstructure nanoglued therein, comprising:
   A. forming a gold~cytochrome c biocomposite superstructure by mixing together 10-nm colloidal gold particles with cytochrome c;
   B. forming a silica sol by mixing together tetramethoxylsilane and aqueous ammonium hydroxide whereby said silane is hydrolyzed to form said silica sol;
   C. forming a silica gel with said gold~cytochrome c superstructure nanoglued therein by mixing together said biocomposite and said silica sol, and allowing said sol to gel;
   D. extracting and supercritically drying said gel with carbon dioxide to form said aerogel with said gold~cytochrome c superstructure nanoglued therein.

* * * * *